(12) United States Patent
Larabee

(10) Patent No.: US 8,727,181 B2
(45) Date of Patent: May 20, 2014

(54) LIQUID DISPENSING DEVICE

(76) Inventor: Eric Stephen Larabee, Bellevue, WA (US)

( * ) Notice: Subject to any disclaimer, the term of this patent is extended or adjusted under 35 U.S.C. 154(b) by 148 days.

(21) Appl. No.: 12/660,115

(22) Filed: Feb. 22, 2010

(65) Prior Publication Data

US 2010/0264168 A1   Oct. 21, 2010

Related U.S. Application Data

(60) Provisional application No. 61/209,655, filed on Mar. 10, 2009.

(51) Int. Cl.
*B67D 7/84* (2010.01)

(52) U.S. Cl.
USPC .......... 222/162; 222/153.04; 222/153.11; 222/156; 220/87.1; 220/87.2; 220/908; 220/908.2

(58) Field of Classification Search
USPC .......... 222/160, 162, 631, 153.01, 153.04, 222/153.11, 153.13, 238, 156–159; 220/908, 908.01, 908.02, 87.5, 908.1, 220/908.2, 87.2, 87.1; 366/156.1
See application file for complete search history.

(56) References Cited

U.S. PATENT DOCUMENTS

| | | | | |
|---|---|---|---|---|
| 1,481,685 A | * | 1/1924 | Burrows | 220/501 |
| 2,281,630 A | * | 5/1942 | Southard | 220/87.2 |
| 2,652,173 A | * | 9/1953 | Farrell | 220/87.2 |
| 3,307,902 A | * | 3/1967 | Nardi | 312/31.3 |
| 3,372,875 A | | 3/1968 | Torrey | |
| 3,636,862 A | * | 1/1972 | Bottas et al. | 100/45 |
| 3,921,857 A | * | 11/1975 | Riccio | 222/145.5 |
| 4,902,482 A | * | 2/1990 | Faust | 422/121 |
| 4,907,747 A | * | 3/1990 | Kim | 239/578 |
| 5,104,230 A | * | 4/1992 | Douche et al. | 366/156.1 |
| 5,170,903 A | * | 12/1992 | Fleming | 220/87.2 |
| 5,366,122 A | * | 11/1994 | Guentert et al. | 222/401 |
| 5,829,642 A | * | 11/1998 | Momboisse | 222/162 |
| 5,964,229 A | * | 10/1999 | Brendel | 134/52 |
| 6,845,888 B2 | * | 1/2005 | Verherbrugghen et al. | 222/162 |
| 7,516,865 B1 | * | 4/2009 | Pierre | 220/87.1 |
| 7,878,359 B1 | * | 2/2011 | Ko | 220/87.2 |

* cited by examiner

*Primary Examiner* — Frederick C Nicolas

(74) *Attorney, Agent, or Firm* — Kilpatrick Townsend & Stockton, LLP

(57) ABSTRACT

Trash receptacles are rarely cleaned. These containers can contain germs and disease in them in many situations. This liquid dispensing device will spray a liquid of choice with in the interior of the trash receptacle automatically every time it is emptied and replaced onto the support surface. These liquids may drastically reduce the amount of bacteria, germs, insects, and disease with in the container. This device will provide this sanitation service automatically. This liquid dispensing device may be attached to industrial dumpsters as well as to residential trash containers. This device does not require a power supply.

11 Claims, 5 Drawing Sheets

US 8,727,181 B2

LIQUID DISPENSING DEVICE

CROSS-REFERENCE TO RELATED APPLICATION

This application claims the benefit of U.S. Provisional Patent Application No. 61/209,655, filed on Mar. 10, 2009, titled "LIQUID DISPENSING DEVICE," the contents of which is hereby incorporated in its entirety by reference.

The claimed invention is directed generally to a trash container spray system, and more particularly, a container spray system for selectively spraying a cleaning material into a commercial trash container.

STATEMENT REGARDING FEDERALLY SPONSORED RESEARCH OF DEVELOPMENT

Not Applicable

REFERENCE TO SEQUENCE LISTING, A TABLE, OR A COMPUTER PROGRAM LISTING COMPACT DISK APPENDIX

Not Applicable

BACKGROUND OF THE INVENTION

The use of large bins or containers for the deposit of trash and/or garbage from commercial establishments and residential apartments has grown substantially. These trash or garbage containers are usually emptied periodically by a front loading dump truck which carries a pair of forwardly extending lift forks that are insert able into pick up sleeves placed on opposed sides of the containers so that the container can be lifted off the ground and its contents dumped into the body of the truck. Since these containers are quite large, they may not be emptied for a substantial period of time such as a week or more in some instances. Because these containers often receive garbage as well as trash, many municipalities have required that the interior of the container be treated periodically with a treating material such as a disinfectant and/or odor suppressor. Even when not required by statute, such treatment of the containers is a desirable service which users of the containers may request form the company which supplies and services the containers.

Most front loading containers are presently sprayed by the driver of the truck who, after the trash or garbage has been emptied, must leave the cab of the truck, unwind a hose attached to a spray tank of insecticide and/or odor suppressor, spray the interior of the container, rewind the hose, and return to the cab of the truck. A suitable spray tank and hose arrangement for performing this task is shown in U.S. Pat. No. 3,372,875 to Torrey. It will be readily apparent that there are a number of drawbacks to the presently available container treatment systems. Since the truck may empty 60 to 100 trash or garbage containers during a single day, the driver must perform this procedure many times. The task soon becomes onerous and often is not performed as thoroughly as it should be. The time involved is also substantial and may consume an additional hour or more which could be spent on servicing other customers. The driver is also subject to repeated exposures to the material being sprayed onto the containers and such exposure is at least unpleasant and may be detrimental to the health of the driver. The customer either must have a spray treatment of the trash containers to comply with local statutes or desires this service for reasons of sanitation, but the driver who must perform the service views it as a time consuming, tiresome, disagreeable chore, thus causing a continuous controversy between the customer and the trash containing servicing contractor over the performance of the service.

BRIEF SUMMARY OF THE INVENTION

There is a need for a system that provides this sanitation service automatically. The claimed invention meets this need with a system that does not require a power supply.

DETAILED DESCRIPTION OF THE INVENTION

Figure 1:
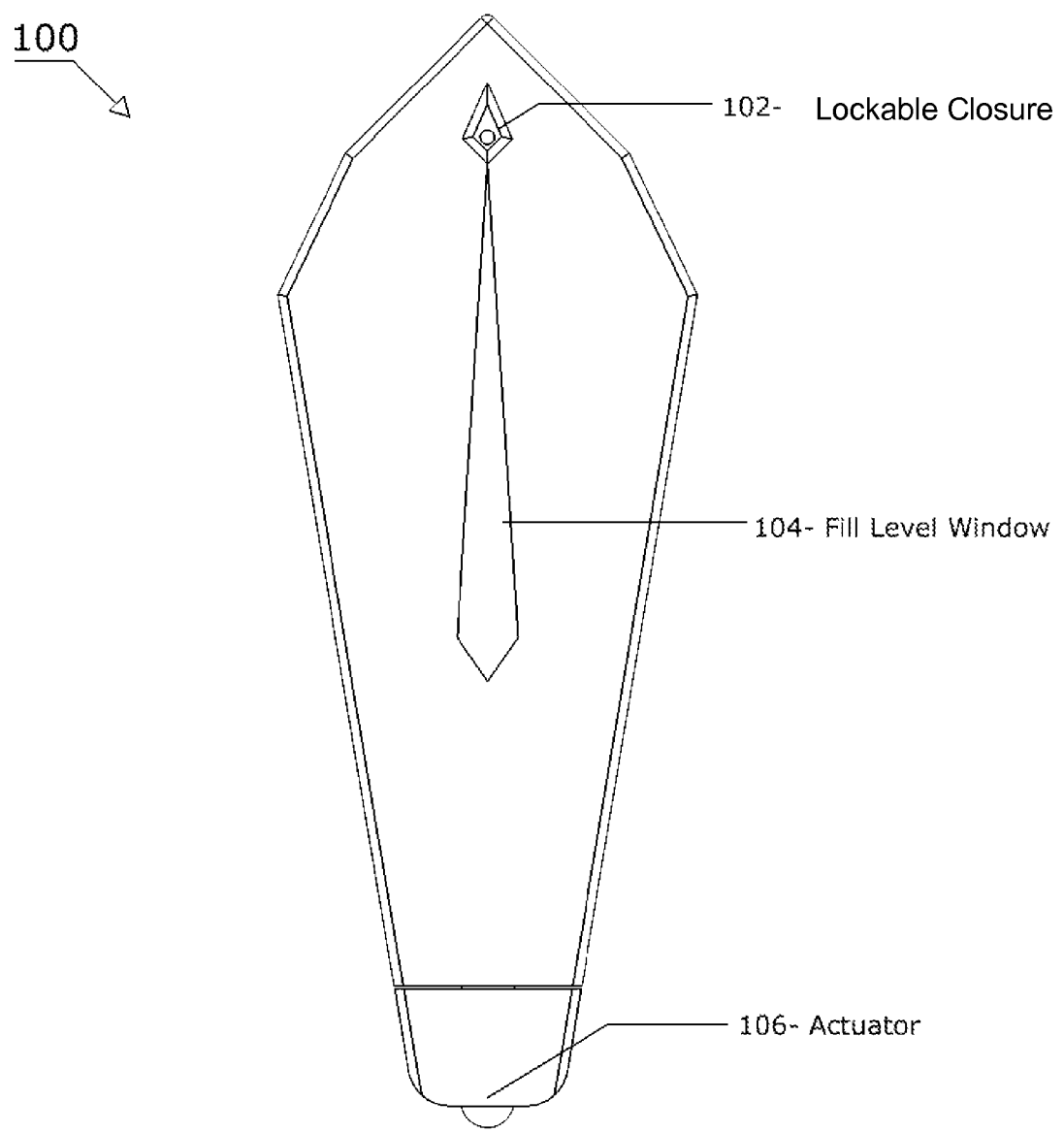
FIG. 1: Liquid dispensing device attached to container, piston and contact plate in first position.
Figure 2:
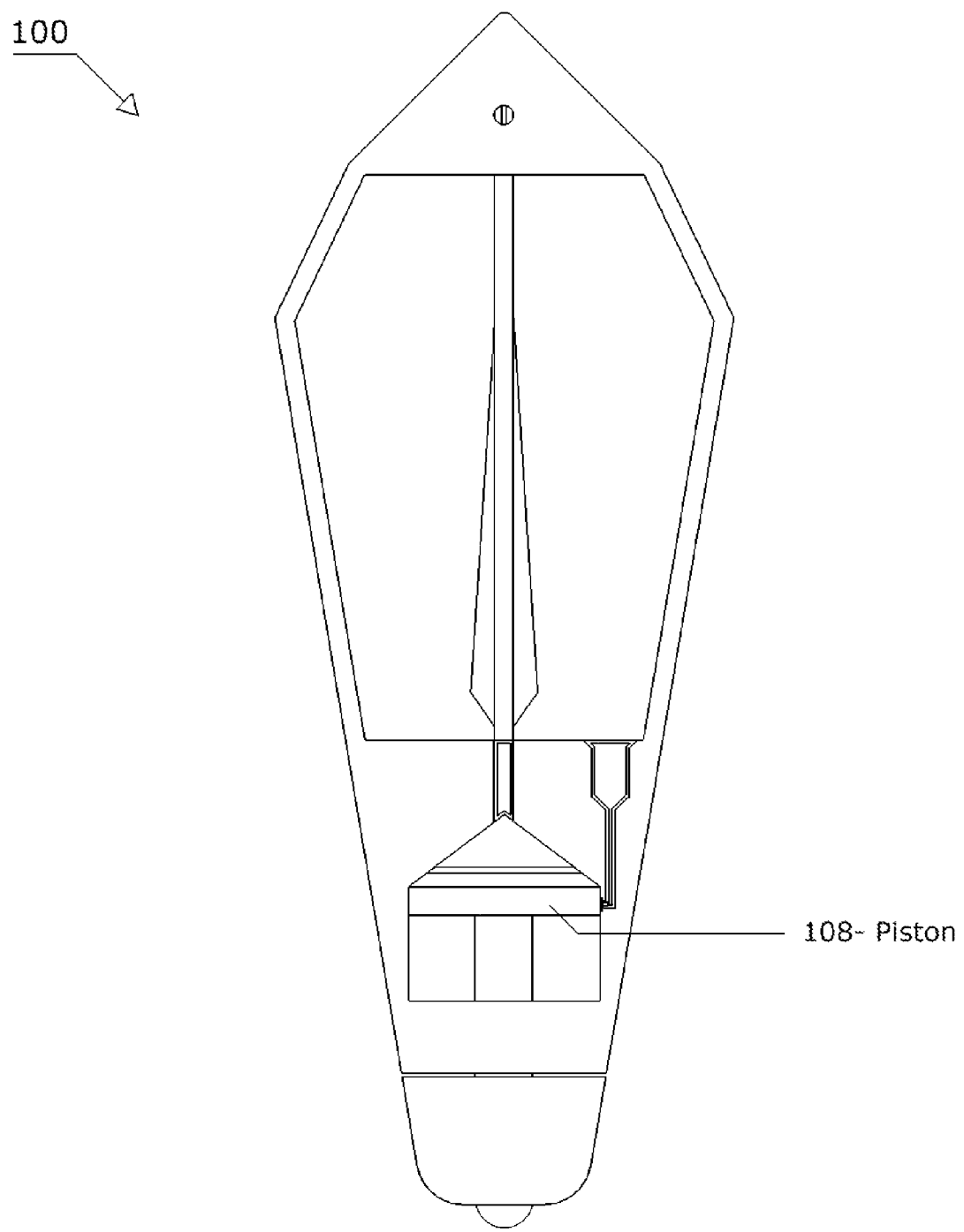
FIG. 2: Trash truck lifts receptacle, device extends piston and contact plate away from the base of the container to its second position when receptacle is removed from the support surface.
Figure 3:
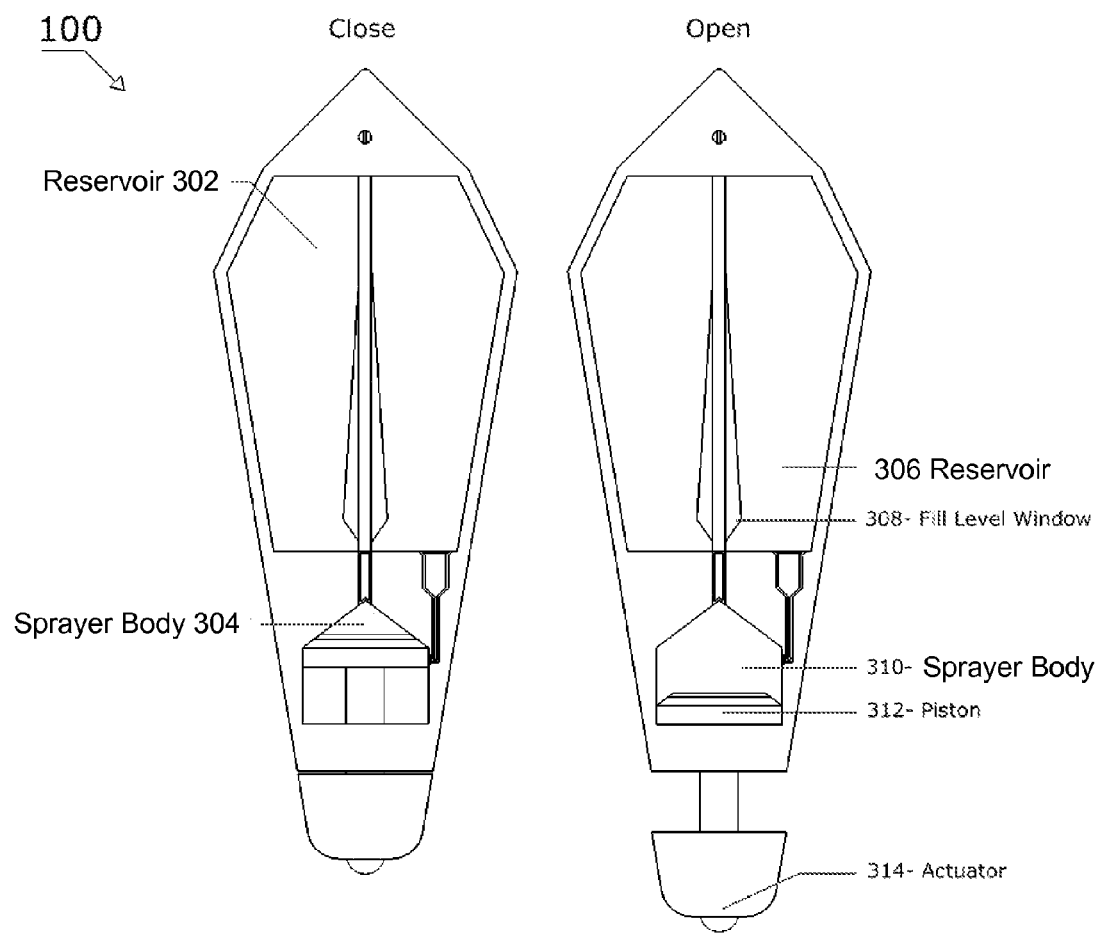
FIG. 3: Devices piston and contact plate retract to its first position when receptacle is returned to the support surface.
Figure 4:
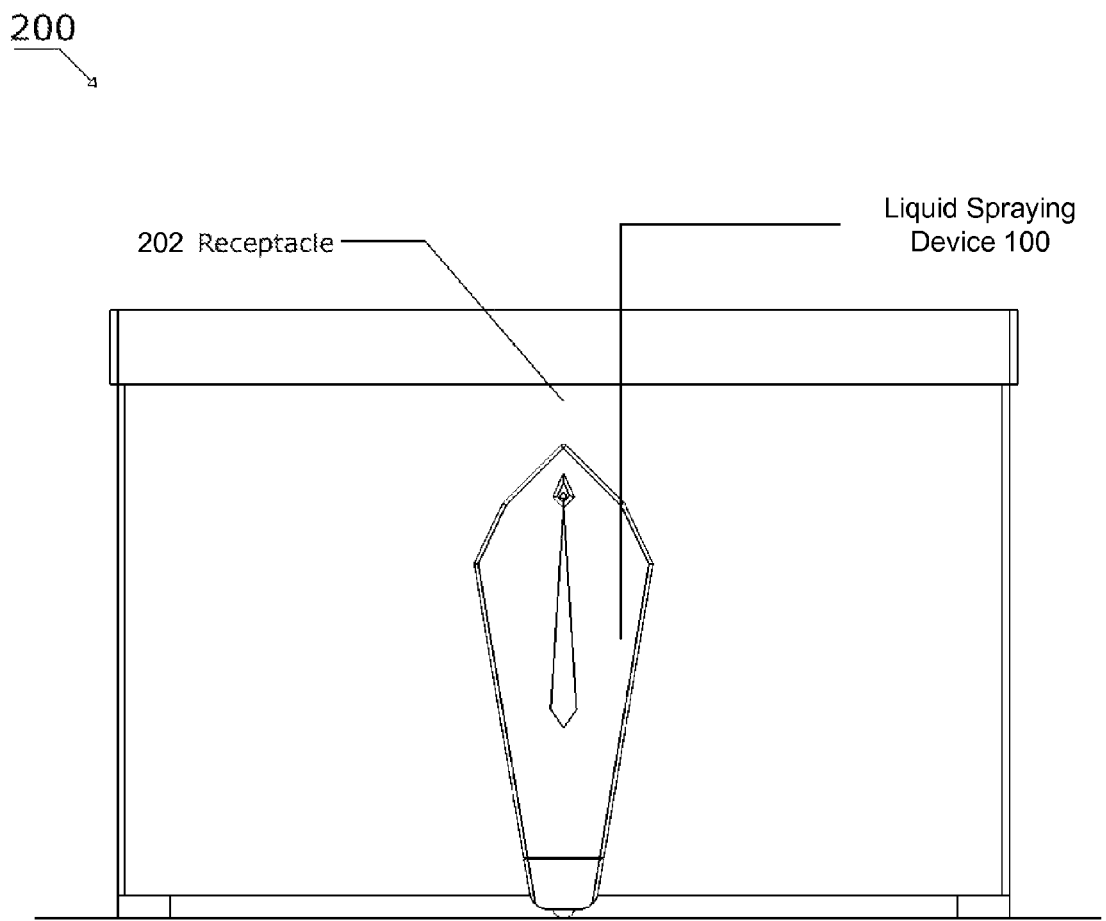
FIG. 4: Liquid is sprayed through nozzle on at least a portion of the interior of the container.
Figure 5:
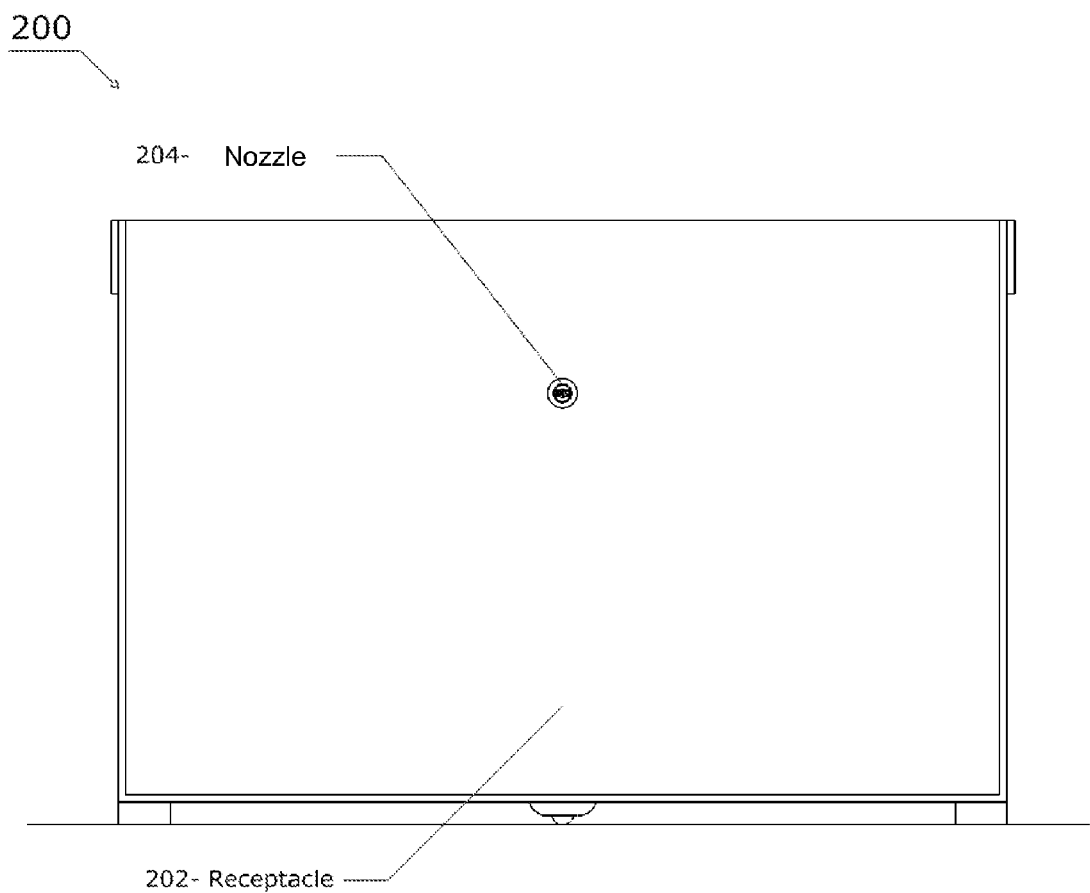
FIG. 5: illustrates a schematic diagram depicting exterior aspects of a nozzle of a sprayer body and receptacle.

It is an object of the claimed invention to provide an improved trash container by adding a spray system to a trash container. The trash container includes a base, a lid arranged opposite the base, and at least one sidewall extending up from the base. The base and lid and sidewall enclose an interior of the container, and the container is shaped and adapted to temporarily hold items for subsequent removal by lifting the receptacle 202 from a support service and upending the receptacle 202. The liquid spraying device 100 comprises a reservoir 302, 306, a sprayer body 304, 310, a nozzle 204, a lockable closure 102, a fill level window 104, 308 and an actuator 106, 314 (FIG. 1). The sprayer body 304, 310 is in liquid communication with the reservoir 302, 306 and the nozzle 204 is in liquid communication with sprayer body 304, 310. The actuator 106, 314 has a piston 108, 312, a biasing mechanism and a contact plate. The contact plate is operatively connected to the piston 108, 312, and the biasing mechanism is operatively connected to the contact plate. The contact plate is shaped and adapted to contact the support surface when the receptacle 202 is placed on the support surface, and the piston 108, 312 and biasing mechanism is shaped and adapted to move between a first and second position. The piston 108, 312 and biasing mechanism are further shaped and adapted to extend the piston 108, 312 and contact plate away from the base of the container when the receptacle 202 is removed from the support surface (FIG. 2), and to retract the piston 108, 312 and contact plate when the receptacle 202 is replaced on the support surface (FIG. 3). The actuator 106, 314 is shaped and adapted to draw liquid from the reservoir 302, 306 into the sprayer body 304, 310 when the piston is moved in a direction from the first position toward the second position and to expel liquid from the sprayer body 304, 310 toward the nozzle 204 when the piston is moved in a direction from the second position toward the first position. The nozzle 204 is shaped and adapted to spray a liquid on at least a portion of the interior of a container or receptacle 202.

What is claimed is:

1. A liquid spraying device for use with a trash dumpster, the trash dumpster including a base and at least one sidewall extending up from the base, the base and sidewall enclosing an interior of the trash dumpster, the trash dumpster being configured to hold items for subsequent removal by lifting the trash dumpster from a support surface and upending the trash dumpster, the liquid spraying device comprising:

a reservoir, a sprayer body in liquid communication with the reservoir, at least one nozzle in liquid communication with the sprayer body, and an actuator having a piston and a biasing mechanism and a contact plate, the contact plate being operatively connected to the piston, the biasing mechanism being operatively connected to the contact plate, the contact plate being configured to contact the support surface of the trash dumpster when the trash dumpster is placed on the support surface, the piston and biasing mechanism being configured to move between a first and second position, the piston and biasing mechanism being further configured to extend the piston and contact plate away from the base of the trash dumpster when the trash dumpster is removed from the support surface and to retract the piston and contact plate when the trash dumpster is replaced on the support surface, the actuator being configured to draw liquid from the reservoir into the sprayer body when the piston is moved in a direction from the first position toward the second position and to expel the liquid from the sprayer body toward the nozzle when the piston is moved in a direction from the second position toward the first position, the nozzle being configured to spray the liquid on at least a portion of the interior of the trash dumpster.

2. A liquid spraying device as set forth in claim 1 further comprising a lockable closure located on the reservoir.

3. A liquid spraying device as set forth in claim 1 further comprising a fill level window located on the reservoir for displaying a current level of the liquid in the reservoir.

4. A trash dumpster spraying device comprising:

a trash dumpster including a base, a lid arranged opposite the base, and at least one sidewall extending up from the base, the base and lid and sidewall enclosing an interior of the trash dumpster, the trash dumpster being configured to hold items for subsequent removal by lifting the trash dumpster from a support surface and upending the trash dumpster; and a liquid spraying device operatively connected to the sidewall of the trash dumpster, the liquid spraying device including a reservoir, a sprayer body in liquid communication with the trash dumpster, at least one nozzle in liquid communication with the sprayer body, and an actuator having a piston and a biasing mechanism and a contact plate, the contact plate being operatively connected to the piston, the biasing mechanism being operatively connected to the contact plate, the contact plate being configured to contact the support surface when the trash dumpster is placed on the support surface, the piston and biasing mechanism being configured to move between a first and second position, the piston and biasing mechanism being further configured to extend the piston and contact plate away from the base of the trash dumpster when the trash dumpster is removed from the support surface and to retract the piston and contact plate when the trash dumpster is replaced on the support surface, the actuator being configured to draw liquid from the reservoir into the sprayer body when the piston is moved in a direction from the first position toward the second position and to expel the liquid from the sprayer body toward the nozzle when the piston is moved in a direction from the second position toward the first position, the nozzle being configured to spray the liquid on at least a portion of the interior of the trash dumpster.

5. A trash dumpster spraying device as set forth in claim 4 wherein the reservoir includes a fill level window for displaying a current level of the liquid in the reservoir.

6. A trash dumpster spraying device as set forth in claim 4 further comprising a lockable closure located on the reservoir.

7. A trash dumpster spraying device as set forth in claim 4 wherein the trash dumpster comprises a commercial trash dumpster configured to be lifted by a trash truck.

8. A method comprising the steps of:

providing a commercial trash dumpster including a base, a lid arranged opposite the base, and at least one sidewall extending up from the base, the base and lid and sidewall enclosing an interior of the commercial trash dumpster, the commercial trash dumpster being shaped and adapted to temporarily hold items for subsequent removal by lifting the commercial trash dumpster from a support surface and upending the commercial trash dumpster; and providing a liquid spraying device being adapted to operatively attach to the sidewall of the commercial trash dumpster, the liquid spraying device including a reservoir, a sprayer body in liquid communication with the reservoir, at least one nozzle in liquid communication with the sprayer body, and an actuator having a piston and a biasing mechanism and a contact plate, the contact plate being operatively connected to the piston, the biasing mechanism being operatively connected to the contact plate, the contact plate being shaped and adapted to contact the support surface when the liquid spraying device is connected to the commercial trash dumpster and the commercial trash dumpster is placed on the support surface, the piston and biasing mechanism being shaped and adapted to move between a first and second position, the piston and biasing mechanism being further shaped and adapted to extend the piston and contact plate away from the base of the commercial trash dumpster when the commercial trash dumpster is removed from the support surface and to retract the piston and contact plate when the commercial trash dumpster is replaced on the support surface, the actuator being shaped and adapted to draw liquid from the reservoir into the sprayer body when the piston is moved in a direction from the first position toward the second position and to expel the liquid from the sprayer body toward the nozzle when the piston is moved in a direction from the second position toward the first position, the nozzle being shaped and adapted to spray the liquid on at least a portion of the interior of the commercial trash dumpster;

and attaching the liquid spraying device to the commercial trash dumpster.

9. A method as set forth in claim 8 further comprising: filling the reservoir with the liquid.

10. A method as set forth in claim 8 further comprising: filling the reservoir with a disinfectant.

11. A method as set forth in claim 8 further comprising: refilling the reservoir with the liquid.

* * * * *